US010927337B2

(12) United States Patent
Forsberg et al.

(10) Patent No.: US 10,927,337 B2
(45) Date of Patent: Feb. 23, 2021

(54) DISPOSABLE CONTAINER, MIXING SYSTEM AND PACKAGING

(71) Applicant: Global Life Sciences Solutions USA LLC, Marlborough, MA (US)

(72) Inventors: Steven James Forsberg, Westborough, MA (US); Ralph Stankowski, Westborough, MA (US); Colin R. Tuohey, Westborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 292 days.

(21) Appl. No.: 15/765,537

(22) PCT Filed: Oct. 11, 2016

(86) PCT No.: PCT/EP2016/074335
§ 371 (c)(1),
(2) Date: Apr. 3, 2018

(87) PCT Pub. No.: WO2017/064058
PCT Pub. Date: Apr. 20, 2017

(65) Prior Publication Data
US 2019/0078046 A1 Mar. 14, 2019

Related U.S. Application Data

(63) Continuation of application No. 14/885,580, filed on Oct. 16, 2015, now Pat. No. 10,836,989.

(51) Int. Cl.
*C12M 1/06* (2006.01)
*C12M 1/00* (2006.01)
(Continued)

(52) U.S. Cl.
CPC ......... *C12M 27/02* (2013.01); *B01F 7/00383* (2013.01); *B01F 7/00633* (2013.01);
(Continued)

(58) Field of Classification Search
CPC ...... C12M 27/02; C12M 27/04; C12M 23/28; C12M 23/14; C12M 23/26; C12M 29/06;
(Continued)

(56) References Cited

U.S. PATENT DOCUMENTS

| 4,162,855 A | 7/1979 | Bender |
| 5,897,012 A | 4/1999 | Sortwell |

(Continued)

FOREIGN PATENT DOCUMENTS

| CA | 2321872 A1 | 9/1999 | |
| DE | 102014101839 A1 * | 8/2015 | ............ C12M 25/06 |

(Continued)

OTHER PUBLICATIONS

European Search Report from EP Appl. No. 19160102.0, dated May 28, 2019.
(Continued)

*Primary Examiner* — Michael L Hobbs
(74) *Attorney, Agent, or Firm* — Eversheds Sutherland (US) LLP

(57) ABSTRACT

A bioreactor system and packaging is provided. The bioreactor system includes a vessel for housing biomaterials for processing and a support structure. The vessel includes a flexible material defining a chamber and a mixing system positioned within the chamber. The mixing system includes an agitator for imparting motion and mixing to the contents of the vessel and includes a base affixed to the flexible material at a base section of the chamber, a shaft moveably mounted in the base and extending from the base into the chamber and at least one mixing element mounted to the shaft, the shaft configured to be driven by a motor magnetically coupled to the shaft and external to the lower portion of the chamber. The support structure is connected to the mixing system such that the shaft is moveable therein and
(Continued)

configured to cooperate with an external structure to provide support for the shaft.

8 Claims, 11 Drawing Sheets

(51) Int. Cl.
    *B01F 7/00*     (2006.01)
    *B01F 15/00*     (2006.01)
    *C12M 1/04*     (2006.01)
    *B65D 61/00*     (2006.01)

(52) U.S. Cl.
    CPC .... *B01F 15/0085* (2013.01); *B01F 15/00668* (2013.01); *B65D 61/00* (2013.01); *C12M 23/14* (2013.01); *C12M 23/26* (2013.01); *C12M 23/28* (2013.01); *C12M 27/04* (2013.01); *C12M 29/06* (2013.01)

(58) Field of Classification Search
    CPC .............. B65D 61/00; B01F 15/00668; B01F 15/0085; B01F 7/00383; B01F 7/0633
    See application file for complete search history.

(56) References Cited

U.S. PATENT DOCUMENTS

| | | | |
|---|---|---|---|
| 6,029,839 | A | 2/2000 | Mansouri |
| 7,384,783 | B2 | 6/2008 | Kunas et al. |
| 7,431,497 | B2 | 10/2008 | Lucas et al. |
| 8,678,638 | B2 | 3/2014 | Wong |
| 2006/0092761 | A1 | 5/2006 | Terentiev |
| 2008/0151683 | A1* | 6/2008 | Meadows ........... B01F 15/0085 366/145 |
| 2011/0013473 | A1* | 1/2011 | Ludwig ............. B01F 15/00831 366/101 |
| 2014/0349385 | A1* | 11/2014 | Erdenberger ........... B01F 7/162 435/302.1 |
| 2016/0333300 | A1* | 11/2016 | Kronenberg ........ B01F 7/00133 |

FOREIGN PATENT DOCUMENTS

| | | | |
|---|---|---|---|
| DE | 102014101839 A1 | 8/2015 | |
| EP | 0174655 A2 * | 3/1986 | ............ B65D 19/20 |
| GB | 2189773 A | 11/1987 | |
| JP | S61-106330 A | 5/1986 | |
| JP | 2012-170364 A | 9/2012 | |
| JP | 2015-043703 A | 3/2015 | |
| WO | 2009116002 A1 | 9/2009 | |
| WO | 2013040161 A1 | 3/2013 | |
| WO | 2013171340 A2 | 11/2013 | |
| WO | 2016107788 A1 | 7/2016 | |
| WO | 2017064058 A1 | 4/2017 | |

OTHER PUBLICATIONS

International Search Report and the Written Opinion of the International Searching Authority, or the Declaration from International Appl. No. PCT/EP2016/074335, dated Apr. 5, 2017.
Chinese Search Report for CN Application No. 201680060123.1 dated May 29, 2020 (19 pages with English tanslation).
Japanese Office Action for JP Application No. 2018-519451 dated Aug. 11, 2020 (7 pages).

* cited by examiner

DISPOSABLE CONTAINER, MIXING SYSTEM AND PACKAGING

BACKGROUND

Various industries are utilizing single-use or disposable systems. Their use continue to rapidly increase, particularly in industries, such as in biopharmaceutical industry, that require use of clean or sterile facilities. Such disposable systems are more flexible and cost-effective than traditional multi-use laboratory and manufacturing facilities that require extensive cleaning and sterilization processes. The components in disposable systems arrive sterilized and having already met to various regulatory requirements.

Disposable systems encompass bioreactors such as microbial bioreactors and fermenters that may include, for example, mixing systems, in which disposable containers or bags are used. The containers or bags are often constructed of sheets of flexible material, such as plastic, plastic laminates or other similar materials.

Disposable mixing systems may involve containers that can be used is a bioreactor system in which cells or microorganisms can grow. The components of such a mixing system can also, for example, be used to prepare buffer and media used in the bioreactor system. Containers can vary in size from a few liters up to several thousand liters in size.

As a result, there is an on-going need in biopharmaceutical development and manufacturing for disposable components that are sterile and easily installed and utilized in, example, a bioreactor system. There is also a need to easily and efficiently ship or transport such disposable components and have them arrive at their destination without having their structure, components or sterility compromised.

BRIEF DESCRIPTION

In another embodiment, a bioreactor system comprises a vessel for housing biomaterials for processing and a support structure. The vessel comprises a flexible material defining a chamber and a mixing system positioned within the chamber. The mixing system comprises an agitator for imparting motion and mixing to the contents of the vessel such that biomaterials contained within the single chamber are mixed and gas bubble circulation is increased, the agitator comprising a base affixed to the flexible material at a base section of the chamber, a shaft moveably mounted in the base and extending from the base into the chamber and at least one mixing element mounted to the shaft, the shaft configured to be driven by a motor magnetically coupled to the shaft and external to the lower portion of the chamber. The support structure is connected to the mixing system such that the shaft is moveable therein and configured to cooperate with an external structure to provide support for the shaft.

In another embodiment, a packaging for storage and transport of a bioreactor system, the bioreactor system having a vessel comprising a flexible material defining a chamber and a mixing system disposed in the chamber, the mixing system including a base and a shaft rotatably mounted in the base. The packaging comprises a frame and a support structure. The frame comprises a base member including a cavity configured in size to have the mixing system base securely positioned therein, vertical support members connected to the base member and cross members connecting adjacent vertical support members. The support structure is connected to the frame and configured to be connected to the shaft of the mixing system.

In another embodiment, a bioreactor system and a packaging for storage and transport thereof comprises a bioreactor system, a packaging and a support structure. The bioreactor system includes a vessel and a mixing system. The vessel is for housing biomaterials for processing and comprises a flexible material defining a chamber. The mixing system is positioned within the chamber and comprises an agitator for imparting motion and mixing to the contents of the vessel such that biomaterials contained within the chamber are mixed and gas bubble circulation is increased. The agitator includes a base affixed to the flexible material at a base section of the chamber, a shaft moveably mounted in the base and extending from the base into the chamber, at least one mixing element mounted to the shaft and a hub in which the shaft is rotatably positioned, the shaft configured to be driven by a motor magnetically coupled to the shaft and external to a lower portion of the chamber. The flexible material also including a plurality of orifices and tubing sections having first and second ends, each orifice connected to the first end of one of the plurality of tubing sections that extends from each opening into the vessel's chamber and the second end is connected to the hub, the connection of the orifice to the first end of the one of the plurality of the tubing sections and of the second end of the one of the plurality of the tubing sections to the hub are capable of substantially preventing fluid leakage. A packaging encloses the bioreactor system and includes a frame. The frame includes a base member including a cavity configured in size to have the mixing system base securely positioned therein, vertical support members connected to the base member and cross members connecting adjacent vertical support members. The support structure includes a plurality of rods having first and second ends connected to the hub of the mixing system at the first end and connected to the frame at the second end to cooperate with the frame to provide support for the shaft, each rod positioned in one of the plurality of tubing sections of the flexible material.

Further suitable embodiments of the invention are described in the dependent claims.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims. Co-pending application WO2016107788 is hereby incorporated by reference in its entirety.

In the process of microbial fermentation, cells may have a short doubling time and as a result of their rapid growth, they consume more oxygen and generate more heat than other mammalian cell applications. As a result, systems that support such an application may include a bioreactor comprising a bag of flexible material with an agitator therein that utilizes a larger agitator motor to drive the agitator that includes multiple impellers mounted to a longer impeller shaft capable of delivering the required power to the fluid. Such a long impeller shaft may need to be stabilized toward the top end of the shaft through a mechanism that connects the tank wall to the impeller shaft inside the bag. The agitator may be driven, for example, through a magnetic coupling with the drive head. The high gas flows within the fermentor necessitate larger filters and a condenser system to preserve the life of the exhaust filters and reduce the volume loss in the bioreactor. The heat transfer surface area is maximized with a jacketed door that results in both high heat transfer surface area and makes bag installation easier.

The present disclosure relates to a vessel (also herein referred to as a container), packaging for the vessel and the vessel and packaging together. The vessel can be a collapsible bag that can perform the role of a container as part of a bioreactor system such as microbial bioreactors and fermenters. The vessel that can be used, for example, as a container in which cells or microorganisms can grow or a container in which liquid constituents utilized in the bioreactor system are prepared and/or stored, such as buffer and media. The bag can be of any size. In one embodiment the collapsible bag may be selected from a two-dimensional bag, a three-dimensional bench top bioreactor bag and a bioreactor, all of which may be sterile and may be disposable or single use. In another embodiment of the invention, the bag is a single use, flexible, nonporous bag. In yet another embodiment of the invention, the vessel can include means for mixing the contents thereof that may be desirable and packaging for the vessel to provide safe and effective transport thereof and, if needed, maintain its sterile status.

Figure 1:
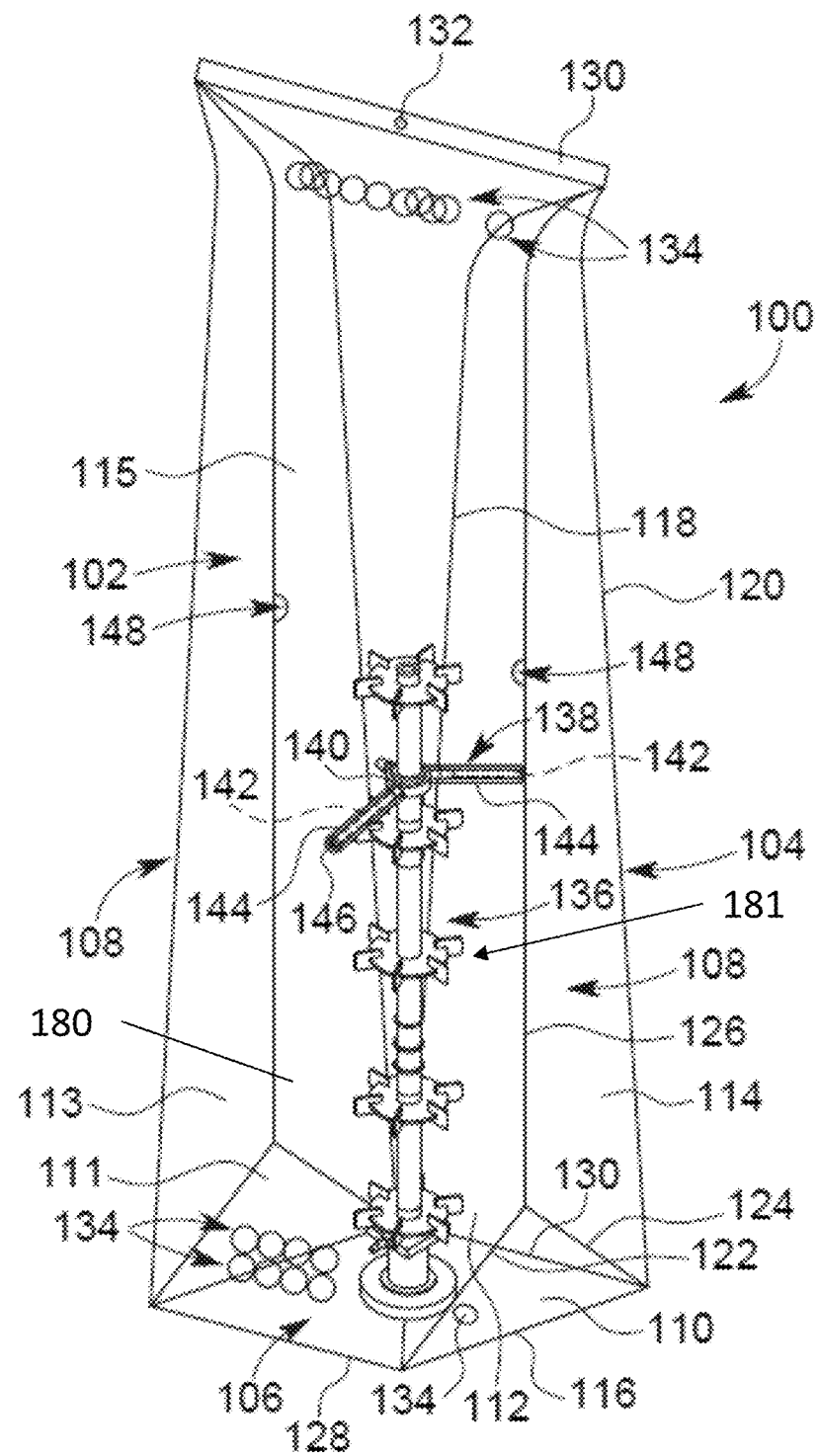
FIG. 1 is a top perspective view of a bioreactor vessel.

FIG. 1—are examples of containers according the present invention.

The skilled person realizes however that for example the vessel or container 100 shown in FIG. 1 may have another form or be of another type as long as the container comprises a side wall, top and bottom, that comprise a flexible material that are joined together to define the container with an interior compartment for keeping a fluid and/or gas inside the container. The vessel may have a volume of from about 10 to about 5000 liters, from about 10 to about 2000 liters preferably. The vessel may also include an internal support structure that cooperates with the vessel. The vessel may also include a flexible container including an agitator (i.e., mixer) to impart motion to the contents thereof during use as shown in FIG. 1. The support structure may also cooperate with packaging in which the container is housed for transport and delivery it place of use.

The flexible material used in the present invention include material that can be easily bent without breaking and may have a thickness of less than 1 mm, suitably of from about 0.005 mm to about 0.7 mm, and preferably of from about 0.01-0.5 mm depending on the size and form of the container or bag. The flexible material may also have a flexural modulus according to ASTM D790 of less than 2000 MPa. The flexibility of such material may also be defined by the thickness of the material, i.e., the thinner the material the more flexible the material. However, two different materials of equal thickness may have different flexibility due to the differences in flexural modulus of the materials. Examples of other parameters typically used for such films are tensile strength of from about 14 MPa to about 18 MPa and elastic modulus of about 370 MPa.

The flexible material may be a polymeric film material and can include a mono layer material or a laminate comprising two or more layers. The flexible material comprises at least one layer of a polymeric film material having thermoplastic properties. The polymeric film material may be sterilizable and preferably gamma radiation resistant in that it substantially retains its properties after exposure thereto. Suitable materials may be conventional polymeric film materials used in the packaging industry, preferably, for example, mono layer or multi-layer PE (polyethylene), ULDPE (Ultra Low Density Polyethylene), LLDPE (Linear Low density Polyethylene), EVOH (Ethylene Vinyl Alcohol) and PA (polyamide). Such film material may also be a laminate film construction that includes one or more polymeric materials or the film material may include, for example, a multi-layer coextruded polyethylene film, such as ULDPE/EVOH/PE/PA. Such a laminate film may be also include two or more material layers, each of the material layers being different thermoplastic materials having different melting points. The flexible materials included here are only meant to be examples of suitable materials. Any flexible material with thermoplastic properties which fulfill the necessary requirements can be used. Preferably, the flexible material includes those used in biotech applications such as polyethylene (PE) with EVOH gas barrier with PE being the inner layer and, thus, in product contact with the contents thereof.

The support structure comprises metal (for example steel or stainless steel) or other rigid or semi-rigid material is meant to include a material which is unbending or may be slightly bent, i.e. may be slightly flexible and/or has elastic properties, and can be polymeric material. The support structure is intended to impart separation between the flexible material and the agitator to, for example, maintain the integrity of the flexible material and reduce the opportunity for the agitator to contact and/or damage the flexible material. The flexural modulus of the rigid material may be greater than 200 MPa according to ASTM D790. The flexural modulus value of the rigid or semi-rigid material may be overlapping with the flexural modulus value of the flexible material, however, the rigidity of the rigid or semi-rigid material may also be affected by the thickness of such material. The rigid material can have a thickness of at least about 1 mm with no upper limit for the thickness of the rigid material. The rigid or semi rigid material should also be substantially dimensionally stable and is preferably moldable. Examples of such suitable materials include low density polyethylene materials; high density polyethylene materials; polyamide; and polypropylene as well as composite materials including a polymer matrix, such as polyester, vinyl ester, polyamide polypropylene or other moldable polymer materials. The polymer material preferably has thermoplastic properties and can be sterilized and preferably resists gamma radiation, i.e. it substantially retains its properties after gamma radiation. The support structure parts comprising rigid or semi-rigid material can be, for example, vacuum formed or molded, for example, by injection molding.

The seal between the separate sections of flexible material can be obtained by several means. The seal should be fluid-tight so that sterile conditions inside the container can be maintained. The seal can be obtained by means of an adhesive, by heat-sealing or by using both heat-sealing and adhesive.

The adhesives used in the adhesive seal are preferably medical grade adhesives. The adhesives can be for example hot-melt adhesives, UV-curable adhesives or solvent-based adhesives. The hot-melt adhesives used should preferably have a lower melting point than the flexible film material so that the flexible film does not melt when the hot-melt adhesive is applied to the material. Examples of adhesives are for example epoxy- or silicone-based adhesives, such as MasterBond X17 and 3M DP8005. Further, for example, adhesive tape could be used.

The heat seal is obtained by bringing the flexible material in contact with heat, so that the thermoplastic component in the material melts and provides the heat seal. The heat seal may be obtained by any suitable manner, which are per se known to the skilled person, for example, hot air welding, conventional heat mold sealing, impulse heat sealing or ultrasonic welding.

FIG. 1 shows an exemplary vessel or container 100 comprising flexible material as well as within the vessel a support structure and means for agitating or mixing the contents of the container. The vessel includes a front panel 102, a back panel 104, a bottom panel 106 and side panels 108, defining a chamber 180. Each side panel 108 may comprise sections 110, 112 and 114. Sections 110, 112 and 114 may be separate from bottom panel 106, front panel 102 and back panel 104, respectively and sealed along seams 116, 118 and 120 respectively or selectively integral to bottom panel 106, front panel 102 and back panel 104, respectively and folded along seams 116, 118 and 120 respectively. In one embodiment sections 110, 112 and 114 are integral to one another and in another embodiment, sections 110, 112 and 114 are sealed along seams 122, 124 and 126. Front panel 102 and back panel 104 may be sealed to bottom panel 106 along seams 128 and 130, respectively. Another alternative is for front panel 102 and sections 112 and 113 to be integral, back panel 104 and sections 114 and 115 to be integral and bottom panel 106 and sections 110 and 111 to be integral, with each of the integral portions connected via adjacent seams. Sections 111, 113 and 115 make up side panel 108 on the left side of the figure. Front panel 102 and back panel 104 may be sealed together to form a top seam 130 of the container, for example, a weld seam. Top seam 130 may also include an aperture 132 or other means to hang, lift or otherwise provide upper support to the vessel in cooperation with an external support and/or lifting structure such as a hoist or winch (not shown).

The front panel 102, back panel 104 and bottom panel 106 may also include orifices 134 suitable to accessing the interior of the container (e.g., an input port, an exhaust port, harvest ports, etc.) or information about the interior of the container. The orifices 134 located in bottom panel 106, for example, may be used as a drain or harvest port when the container is used as a bioreactor. Suitable connectors can be incorporated with orifices 134 in order to attach, for example, connectors such as, barbed tubing fitments (ports) that can be heat welded to the flexible material. Such connectors may be used to attach, for example, fluid conduits (e.g., an input conduit, an exhaust conduit, an harvest conduit, etc.) filters, probes and sensors that may be in turn attached to tubing (for example, flexible tubing) or in the case of probes and sensors may be stand alone or be connected to systems that can collect information obtained by the probe or sensor. Also included in the container is an agitator for imparting motion and mixing to the contents of the container when it is in use. The agitator 181 may include an impeller 136 which will be described in more detail subsequently. The container may also include a support structure 138 to stabilize impeller 136. The support structure 138 may include a stabilization hub 140 that surrounds the impeller 136 and permits motion of the impeller 136 therein. The stabilization hub 140 may be connected to rods 142. By rod is meant a slim substantially cylinder-shaped shaft construction, which may be hollow or solid and is made of rigid or semi-rigid material. Each rod 142 is enclosed in tubing 144 that may be made of the same or different flexible material as the container. Each of the tubing 144 extends from orifice 146 to which it is attached by, for example, sealing to the stabilization hub 140 to which it is also attached to prevent fluid leakage from inside the container. Each side panels 108 may also include a tab with an aperture 148 for attaching, for example, a hook in order to lift container 100. For example, the apertures in tabs 148 can aid in the installation of the container 100 into a bioreactor tank. A latched S-hook may be inserted into each of the two apertures of tabs 148, the S-hooks connected to a sling that allows an operator to lift the bag when installing into the bioreactor tank. Once inside the tank, an S-hook is inserted through aperture 132 in top seam 130 in order to lift the remaining portion of the bag to the top of the bioreactor tank.

Figure 2:
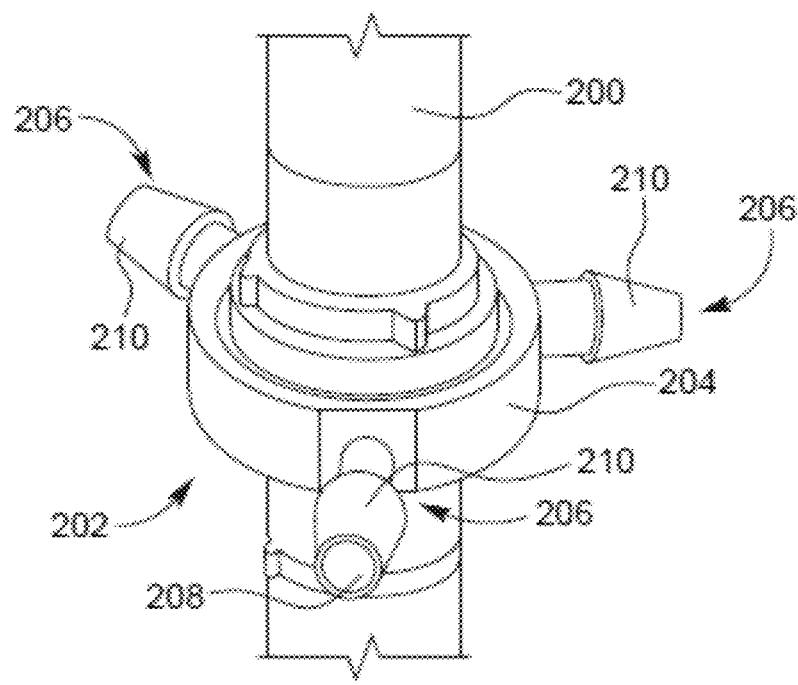
FIG. 2 is a top perspective view of a stabilization hub.

An embodiment of the stabilization hub 140 in FIG. 1 is shown in FIG. 2. FIG. 2 includes the impeller shaft 200 which is rotatably positioned in stabilization hub 202. Stabilization hub 202 includes a collar 204 and connectors 206 equally spaced around the circumference of collar 204. Although the embodiment of FIG. 2 includes 3 connectors 206 for incorporating 3 rods into stabilization hub 202, that number is only meant to be exemplary. Preferably, at least 3 rods are connected to stabilization hub 202. Each of the connectors 206 may include a rod aperture 208 into which a rod, similar to rods 142 in FIG. 1, is slid into position and a barb 210 over which tubing, for example, similar to tubing 144 in FIG. 1, is slid over in order to prevent the tubing from coming off and sealing the tubing to prevent fluid leakage from inside the container.

Figure 3:
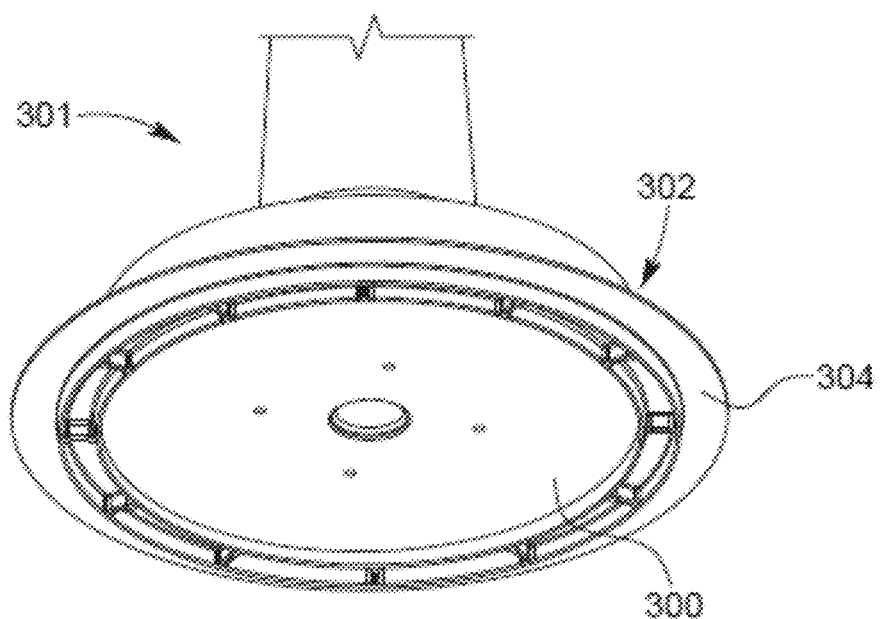
FIG. 3 is a bottom perspective view of a base of an impeller assembly.

FIG. 3 shows an exemplary bottom 300 of the impeller assembly 301 that is positioned closest to the bottom panel 106 in FIG. 1. Impeller assembly 301 includes an impeller base 302 with a lip 304, the latter which is attached to the flexible material of the bottom panel 106 in FIG. 1. This molded impeller base is thicker than the flexible material that makes up the envelope of the container and is made of rigid or semi-rigid material, for example, high density polyethylene. The bottom 300 of the impeller assembly 301 includes an assembly that permits rotation of the impeller in impeller base 302, for example, containing ceramic bearings and a part called a bearing carrier which clips on to the impeller base and keeps the impeller positioned with respect to the impeller base. The bearing assembly at the bottom of the impeller assembly 301 allows the impeller to rotate about the impeller axis when secured to the molded impeller base 302 but is prevented from moving up or down along the impeller axis toward or away from the impeller base. The molded impeller base 302 is attached to the flexible material by, for example, heat welding the lip 304 of the molded impeller base 302 to the flexible material.

The structure connected to, for example, the stabilization hub 140 in FIG. 1, e.g., the rods 142, should impart separation between the flexible material and the agitator to, for example, maintain the integrity of the flexible material and reduce the opportunity for the agitator to contact and damage the flexible material. The stabilization hub 140 may be positioned anywhere along the length of the impeller, but preferably above the middle of the length of the impeller, more preferably above ⅔ from the end of the impeller assembly adjacent the bottom panel 106 in FIG. 1.

Figure 4:
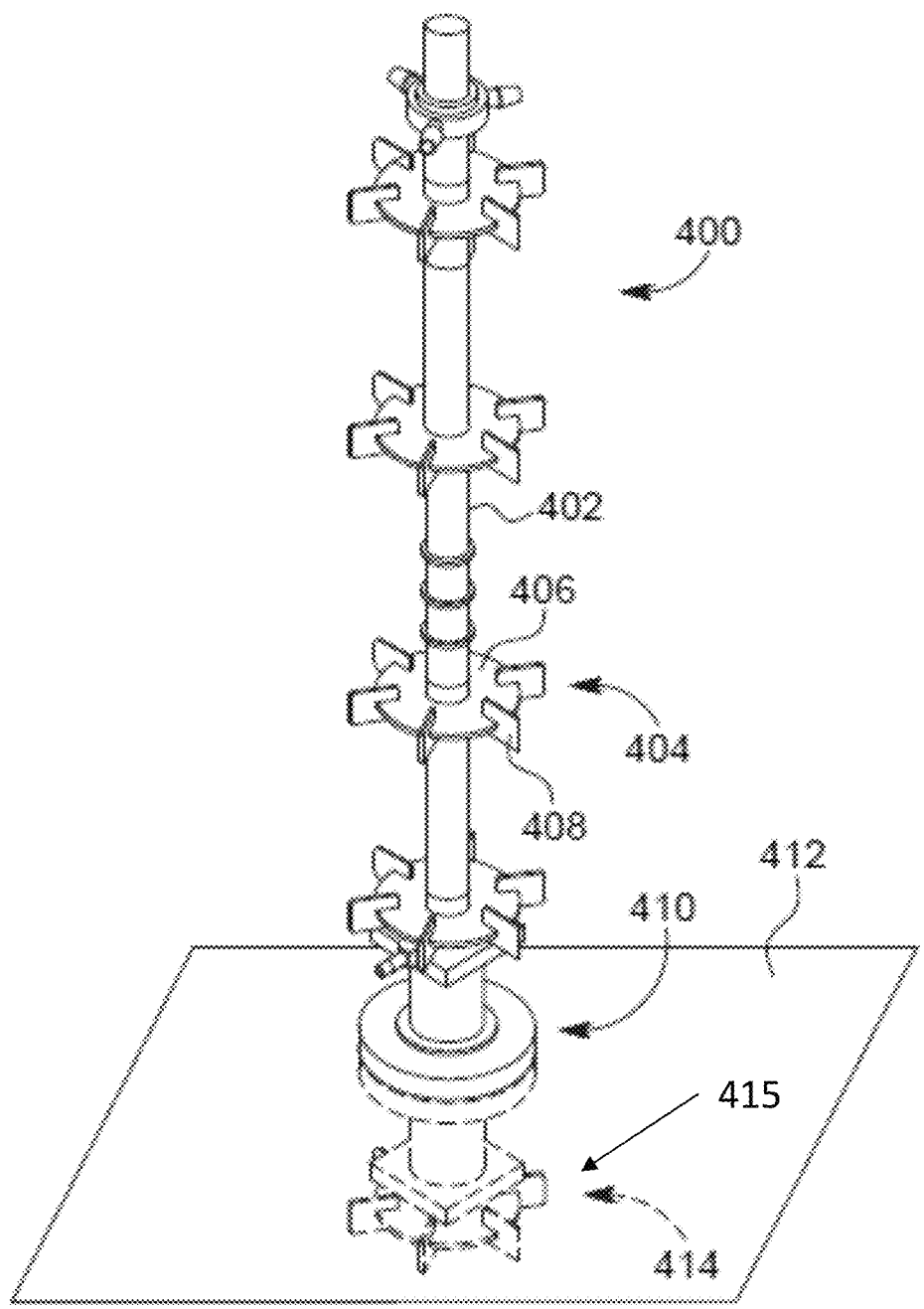
FIG. 4 is a top perspective view of an agitator.

FIG. 4 shows an exemplary agitator comprising an impeller and drive mechanism for the agitator. The impeller 400 includes a shaft 402 and at least one mixing element 404. The mixing element 404 comprises, for example, a collar 406 which is fixed to impeller shaft 402 and at least one blade 408 fixed to the collar 406. Blade 408 can be of a suitable size, shape and angular position relative to the axis of impeller shaft 402 to provide agitation to a surrounding fluid upon rotation of impeller shaft 402 and the resulting movement of mixing elements 404. The impeller shaft 402 is connected to an impeller hub housed in an impeller assembly, the latter housed in a molded impeller base 410 such that the impeller shaft 402 is freely rotatable within the impeller assembly around the axis of the impeller shaft 402. In this exemplary embodiment, molded impeller base 410 is secured to the flexible material of a base panel 412, as described previously. The impeller hub is engaged with a drive mechanism 414 positioned adjacent molded impeller base 410 on the opposite side of the flexible material of base panel 412. The drive mechanism 414 includes a housing with a motor 415 therein, the motor connected to a motor hub, the latter being freely rotatable. The positioning of the drive mechanism 414 relative to molded impeller base 410 and impeller assemble and impeller hub house therein is such that magnets included in the impeller hub interact with the motor and motor hub of drive mechanism 414 and permit the motor to drive the impeller hub through magnetic attraction and, as a result, drive the impeller shaft 402 and mixing element 404 attached thereto.

The packaging for the vessel or container is designed to provide support and protection to the container and the components thereof including the flexible material, impeller and support structure. For example, packaging structure is provided to hold and stabilize the impeller so as to minimize contact between the impeller and flexible material where such contact could result in damage to the flexible material caused by the impeller as well as hold and secure the impeller to minimize movement of the impeller during transit that would result in damage to, for example, the impeller itself or the flexible material.

The packaging may include, for example, wall sections, connected panels or an open frame structure including various connected support members such as vertical members and cross members. Such support members and panels can be joined using various means including interlocking (such as tongue in pocket), sealing, welding or acceptable mechanical means such as suitable mechanical fasteners, such as nut-bolt combinations, rivets, screws, nails, etc. Support members may have, for example, a square, rectangular, circular or oval cross-section.

Figure 5:
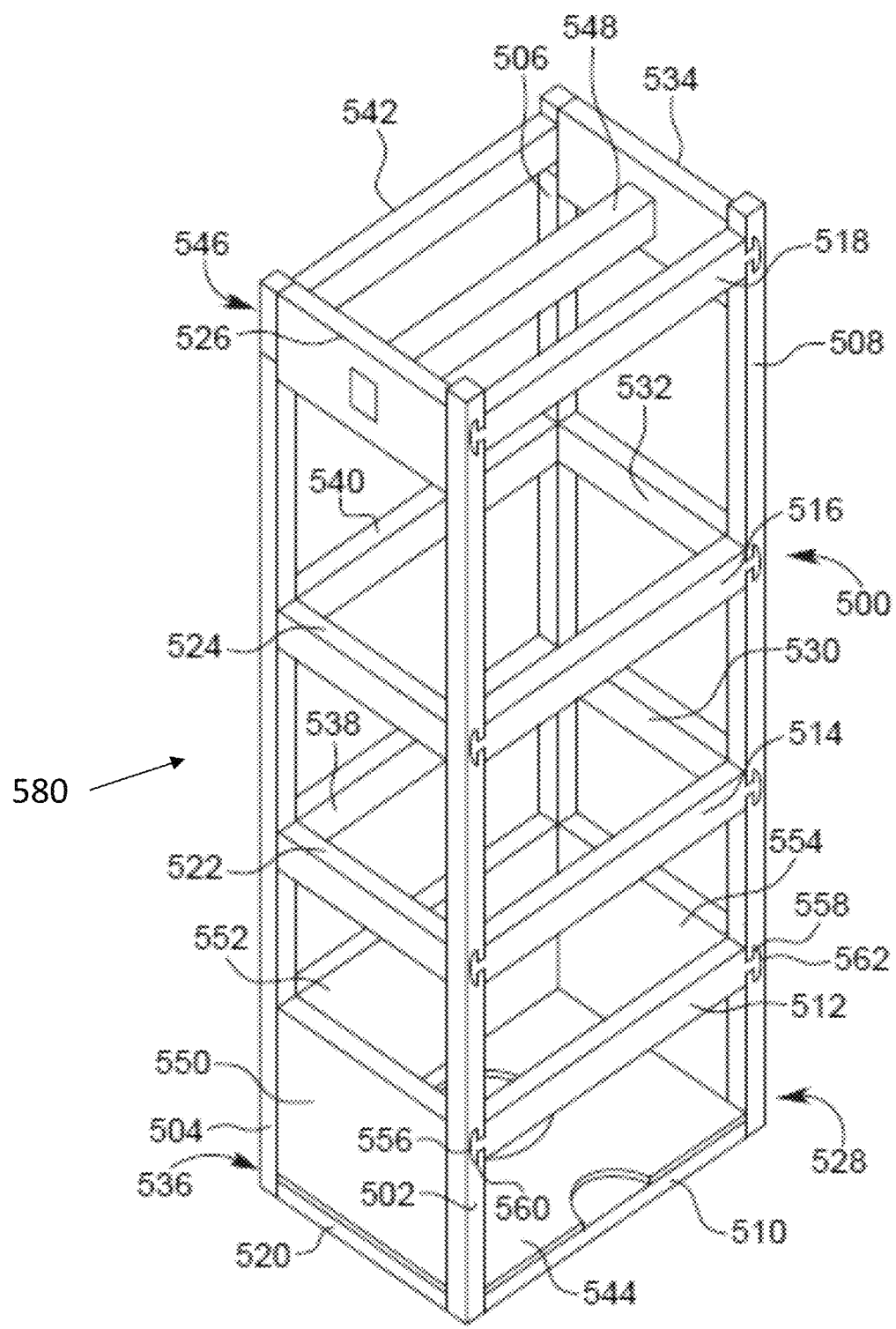
FIG. 5 is a top perspective view of an open frame structure.

One exemplary embodiment of packaging 580 is shown in FIG. 5 includes an open frame structure 500 composed of, for example, foam or other similar rigid or semi-rigid material, such as, for example, crosslinked polyethylene polymer including Vizion™ 4.0 (Rubberlite Inc) and Plastazote® LD60 (Zotefoams plc). The open frame structure may be constructed of crosslinked foam that is clean room compatible and may include multiple vertical support members connected with multiple cross members. In the exemplary embodiment, there are 4 vertical support members 502, 504, 506 and 508 that are connected by 4 front cross members 512, 514, 516 and 518, 3 left side cross members 522, 524 and 526, 3 right side cross members 530, 532 and 534, and 3 back cross members 538, 540 and 542. The 4 vertical support members 502, 504, 506 and 508 are connected to a base member 544 at one end defining a bottom section with the other end defining a top section 546 of the open frame structure 500. Base member 544 includes front side 510, left side 520, right side 528 and back side 536.

Although 4 adjacent cross members (one front, one left side, one right side and one back) in the embodiment are shown to connect to the vertical members at adjacent positions along the length of the vertical support members, it is not necessary that 4 adjacent cross members all occupy the same positions along the vertical support members' length (i.e., they may be offset relative to the over adjacent cross members). However, it is preferred that some of the cross members be substantially parallel to the base member. Preferably, the top section 546 of the open frame structure may also include a central cross member 548. Central cross member 548 may include a tongue portion at each end that are inserted into complementary pockets in side cross members 526 and 534 and affixed therein using, for example, heat welding. In one embodiment, when a container is positioned in the open frame, the top portion of the container, including, for example, seam 130 and adjacent portions of the flexible material of container 100 in FIG. 1, are folded over central cross member 548 so as to support the vessel and minimize the flexible material from sagging onto the agitator housed therein. The open frame structure may also include side panels 550, 552 and 554 to provide additional structural support and are positioned between vertical members 502, 504, 506 and 508 and adjacent the base member 544.

Left side cross members 522, 524 and 526, right side cross members 530, 532 and 534, and back cross members 538, 540 and 542 may be integral to the 4 vertical support members 502, 504, 506 and 508 or connected, for example, using complementary interlocking features included in adjacent members (e.g., tongue in pocket) or by various sealing or adhesive techniques. For example, front cross member 512, may include tongues 556 and 558 that fit into complementary shaped pockets 560 and 562 in vertical support members 502 and 508 to provide a snug fit yet can be separated. Similar attachment means can be used for other cross member, for example, front cross members 514, 516, and 518 to vertical support members 502 and 508 as well as central cross member 548 to left side cross member 526 and right side cross member 534.

Figure 6:
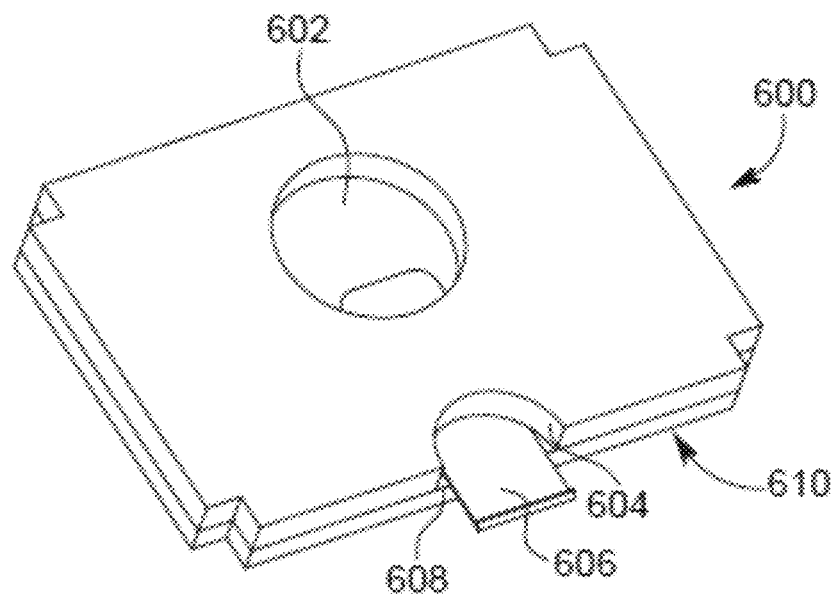
FIG. 6 is a top perspective view of a base member of an open frame structure.

An exemplary embodiment of the base member 544 in FIG. 5 is shown in FIG. 6. FIG. 6 shows base member 600 that includes a circular cavity 602 in which the bottom of an impeller (agitator) housed in the flexible material container rests. Base member 600 also includes a cut-out 604 (e.g., a semi-circular cut in the exemplary embodiment) on the side of base member 600 that faces the front side of the open structure. Once the impeller is positioned in the circular cavity 602, a slide clip 606 is slid into slot 608 from the front side 610 of base member 600 underneath cut-out 604 through a slot connecting cut-out 604 to circular cavity 602 into position in circular cavity 602 under the bottom of the impeller. The slide clip 606 utilizes the magnetic properties of the impeller base (that, when is use, will interact with the drive motor and drive the motion of the agitator) to be attached to and hold the bottom of the impeller in place to stabilize the impeller base. For example, in the event that the packing was to fall over, the slide clip with the magnetic base holds the impeller base in place and protects the bag film.

Figure 7:
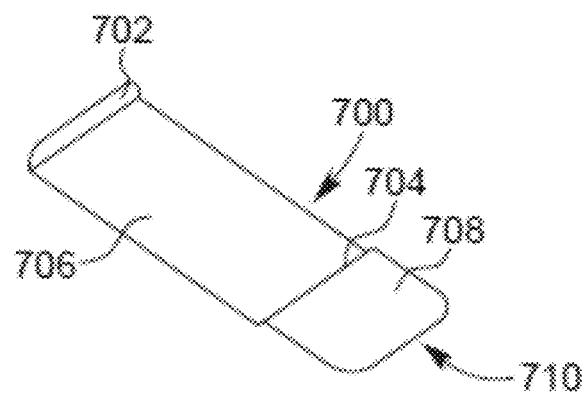
FIG. 7 is a top perspective view of a slide clip.

An exemplary embodiment of the slide clip 606 is shown in FIG. 7. Slide slip 700 includes ridges 702 and 704 with a first planar section 706 between ridges 702 and 704 and a second planar section 708. The second planar section 708 may be positioned using the first planar section 706 and ridge 702 such that the second planar section 708 is positioned in circular cavity 602 of base member 600 shown in FIG. 6 and magnetically secures the base of an impeller positioned in the circular cavity of a base member as described previously. Therefore, side 710 of slide clip 700 is slid into the slot of the base member.

The rods utilized in the support structure may the same or different depending on whether the container is being sterilized, shipped or in use as a bioreactor. For example, during sterilization, the rods may be a material that does not interfere (e.g., cause shadowing) during the sterilization process, for example, polypropylene. The rods utilized during sterilization can be utilized during the shipping process or replaced with other rods, such as, for example, stainless steel rods, that can be used when the container is in operation as a bioreactor.

Figure 8:
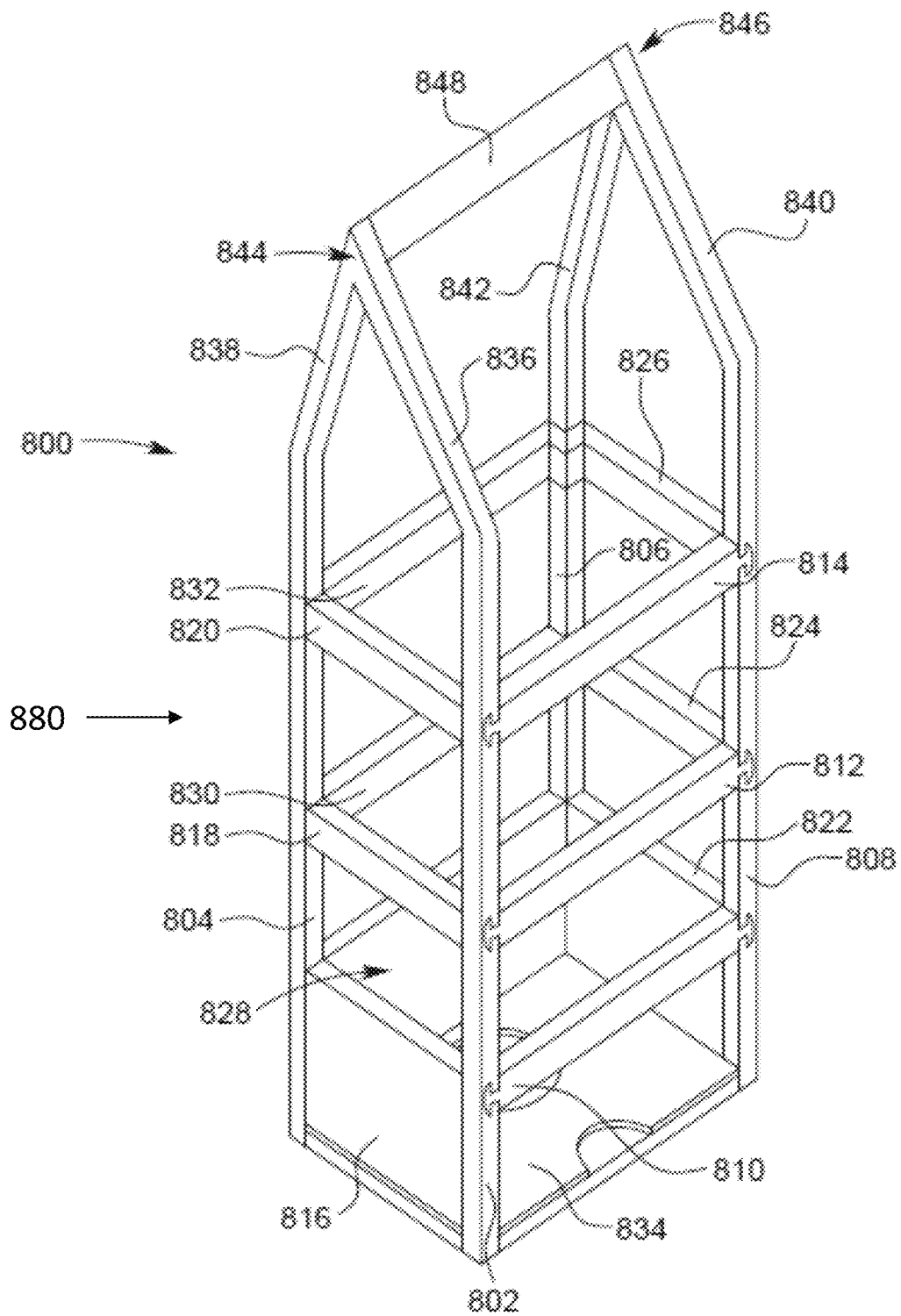
FIG. 8 is a top perspective view of another open frame structure.

Another exemplary embodiment of the open frame structure is composed of similar rigid or semi-rigid material, including foam as shown in the packaging embodiment 880 of FIG. 8. Open frame structure 800 includes 4 vertical support members 802, 804, 806 and 808 that are connected by 3 front cross members 810, 812 and 814, 2 left side cross members 818 and 820, 2 right side cross members 824 and 826 and 2 back cross members 830 and 832. The 4 vertical support members 802, 804, 806 and 808 are connected to a base member 834 at one end defining a bottom section. The open frame structure may also include side panels 816, 822 and 828 to provide additional structural support and are positioned between vertical members 802, 804, 806 and 808 and adjacent the base member 834. A top section that includes front left angled support 836 connected to vertical support members 802, rear left angled support 838 connected to vertical support members 804, front right angled support 840 connected to vertical support members 808 and rear right angled support 842 connected to vertical support members 806. The ends of front left angled support 836 and rear left angled support 838 opposite to the respective vertical members to which each is attached are connected to each other at 844. The ends of front right angled support 840 and rear right angled support 842 opposite to the respective vertical members to which each is attached are connected to each other at 846. A central cross member 848 is connected to angled support members 836, 838, 840 and 842 at positions 844 and 846 as shown. As an alternative, such members and supports may be formed to have any two adjacent elements integral with one another rather than being connected.

Although adjacent cross members (one front, one left side, one right side and one back) in the embodiment are shown to connect to the vertical members at adjacent positions along the length of the vertical support members, it is not necessary that 4 adjacent cross members all occupy the same positions along the vertical support members' length (i.e., they may be offset relative to the over adjacent cross members). Also, members are connected, for example, using complementary interlocking features included in adjacent members or by various sealing or adhesive techniques. Other structural details disclosed for the embodiment of FIG. 5 may also applicable to the embodiment of FIG. 8.

Figure 9:
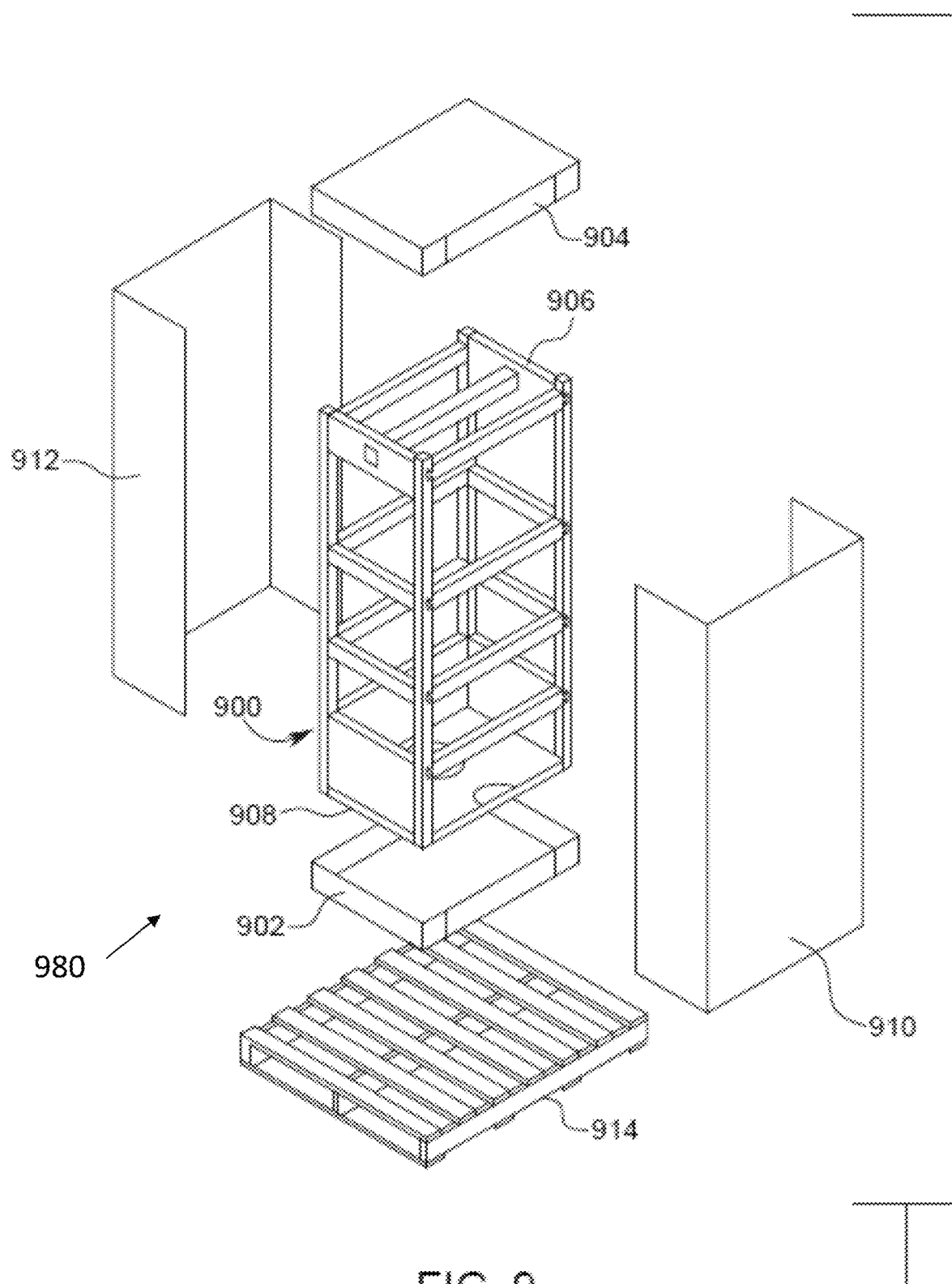
FIG. 9 is a top perspective exploded view of a packaging structure.

The packing/packaging 980 of FIG. 9 comprises packing materials and open frame structure 900. Open frame structure 900 is configured to house an aforementioned container. Various components (e.g., feed lines, tubing, probe and sensor lines) attached to the container positioned in open frame structure 900 may be secured using various attachment means including, for example, cable ties. Open frame structure 900 may be covered with, for example, one of two layers of plastic, such as about a 4 mil to about a 6 mil (about 0.004 to about 0.006 inches or about 100-150 micrometers) clear polypropylene bag including, for example, double bagged in which each is, for example, a polypropylene bag. The plastic covering may include an inner pouch and an outer pouch that cover the open foam frame (e.g., a double bag enclosure). As a result of the exemplary double bag enclosure (or other multi-bag enclosure) around the open frame structure, the bagged open frame structure with the vessel helps facilitate easily passing of the entire assembly through a material airlock and to a clean-room housing the bioreactor, thus minimizing damage to the vessel due to handling. Other open frame structures can be incorporated such as the embodiment of open frame structure 500 in FIG. 5 and the embodiment of an open frame structure 800 in FIG. 8. Additional packing material are shown in FIG. 9 and include a bottom corrugate tray 902 and top corrugate tray 904 that, when assembled, are positioned adjacent the top section 906 and base section 908 of open frame structure 900. The packing material may also include C-fold corrugate sleeves 910 and 912 and are positioned around the area of open frame 900 that is exposed after bottom corrugate tray 902 and top corrugate tray 904 are in position. Also shown is shipping pallet 914 on which bottom corrugate tray 902 may be supported and/or attached. Shipping straps (not shown) may then be used to secure the assembled open frame structure 900 (including container, not shown), plastic covering (if needed), bottom corrugate tray 902, top corrugate tray 904 and C-fold sleeves 910 and 912 to shipping pallet 914.

Figure 10:
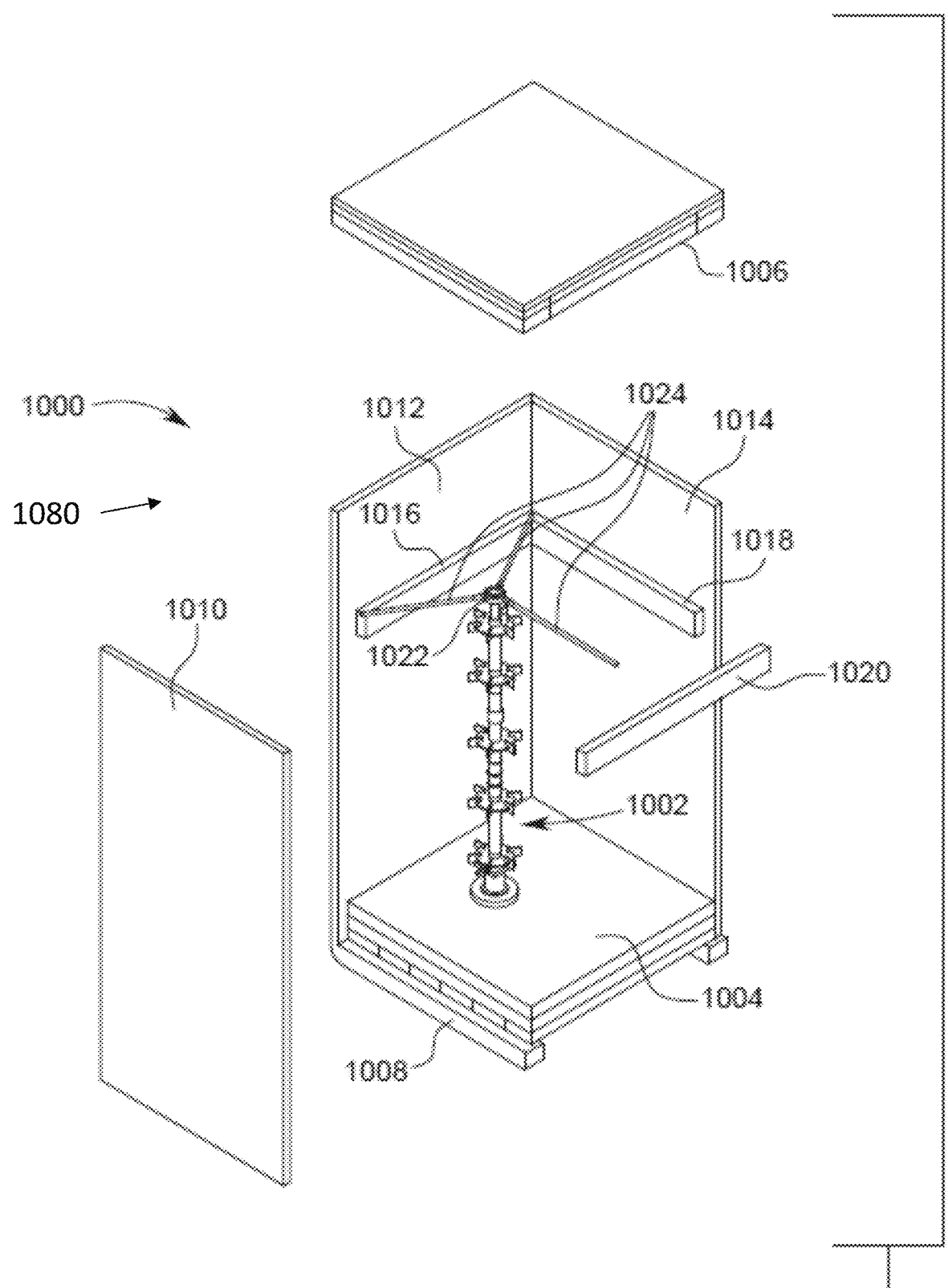
FIG. 10 is a top perspective exploded view of another packaging structure.
Figure 11:
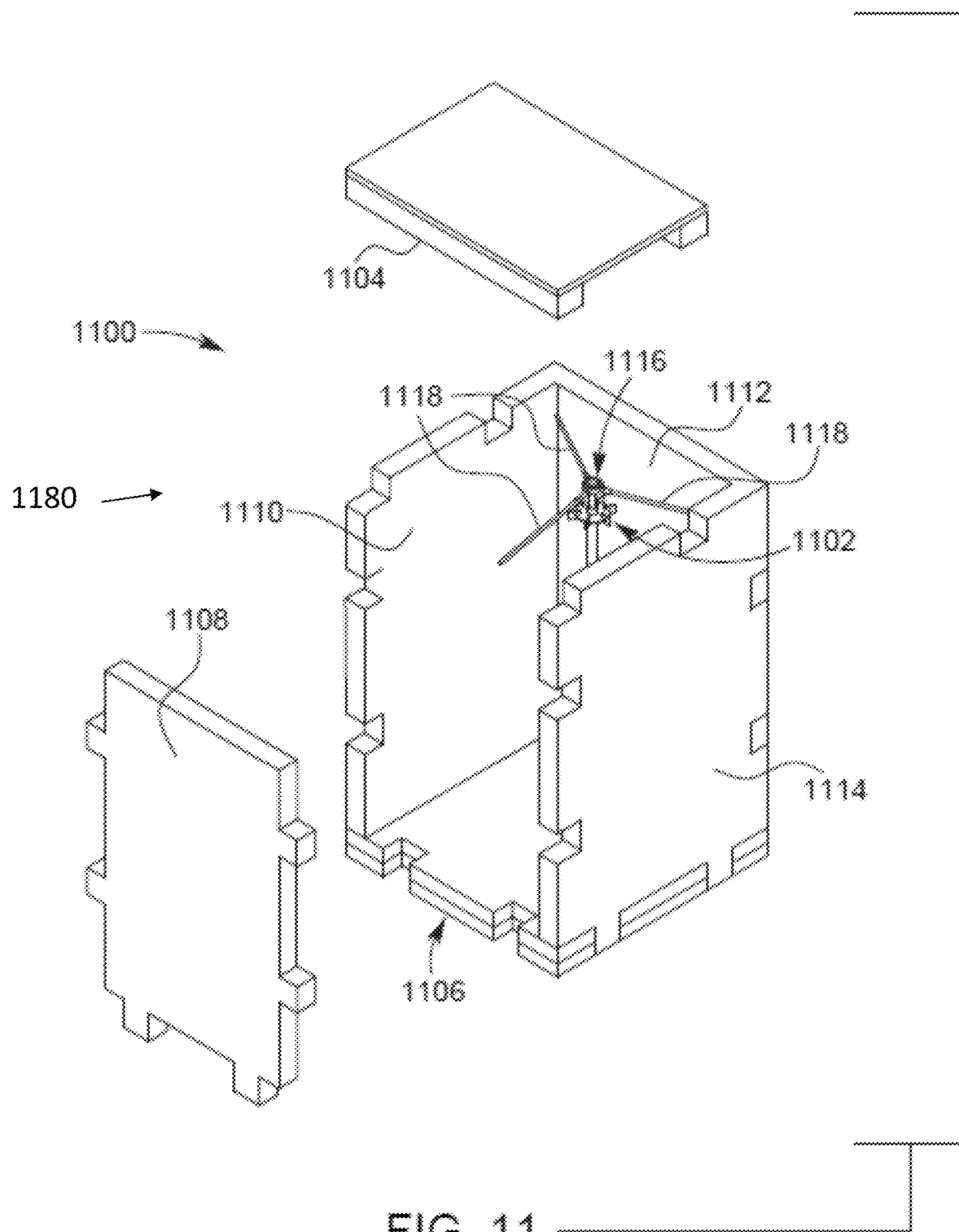
FIG. 11 is a top perspective exploded view of yet another packaging structure.

Other alternative packing/packaging 1080; 1180 can include the embodiments shown in FIG. 10 and FIG. 11. The embodiments of FIG. 10 and FIG. 11 are shown with an agitator and without the container in which the agitator is housed in order to show the interaction between the agitator, support structure and packing shown in the figures. In practice, an embodiment of the aforementioned vessel of flexible material and its various components would be included. FIG. 10 shows packing 1000 for agitator 1002 is positioned on base 1004 which includes a cavity in which the bottom of an agitator is placed. Packing 1000 also includes a top section 1006, a bottom section 1008 on which base 1004 is positioned, 4 side sections, 3 of which are shown: 1010, 1012 and 1014. The fourth side section is structured similarly to 1010, 1012 and 1014. Side sections 1012 and 1014 also include struts 1016 and 1018. Strut 1020 is connected to the fourth side section, not shown. Struts 1016, 1018 and 1020 are positioned adjacent each other and are attached to support structure 1022 via rods 1024. Strut 1020 is positioned on the fourth side section similarly to where struts 1016 and 1018 are positioned on side sections 1012 and 1014. Side section 1010 may also include a strut similar in structure to struts 1016, 1018 and 1020 and positioned similarly where struts 1016 and 1018 are positioned on side sections 1012 and 1014. Support structure 1022 is connected to agitator 1002.

FIG. 11 shows packing/packaging 1100 for agitator 1102. Packing 1100 also includes a top section 1104, bottom section 1106 on which agitator 1102 is positioned, 4 side sections 1108, 1110, 1112 and 1114. Support structure 1116 is connected to the side sections via rods 1118. Support structure 1116 is connected to agitator 1102.

Figure 12A:
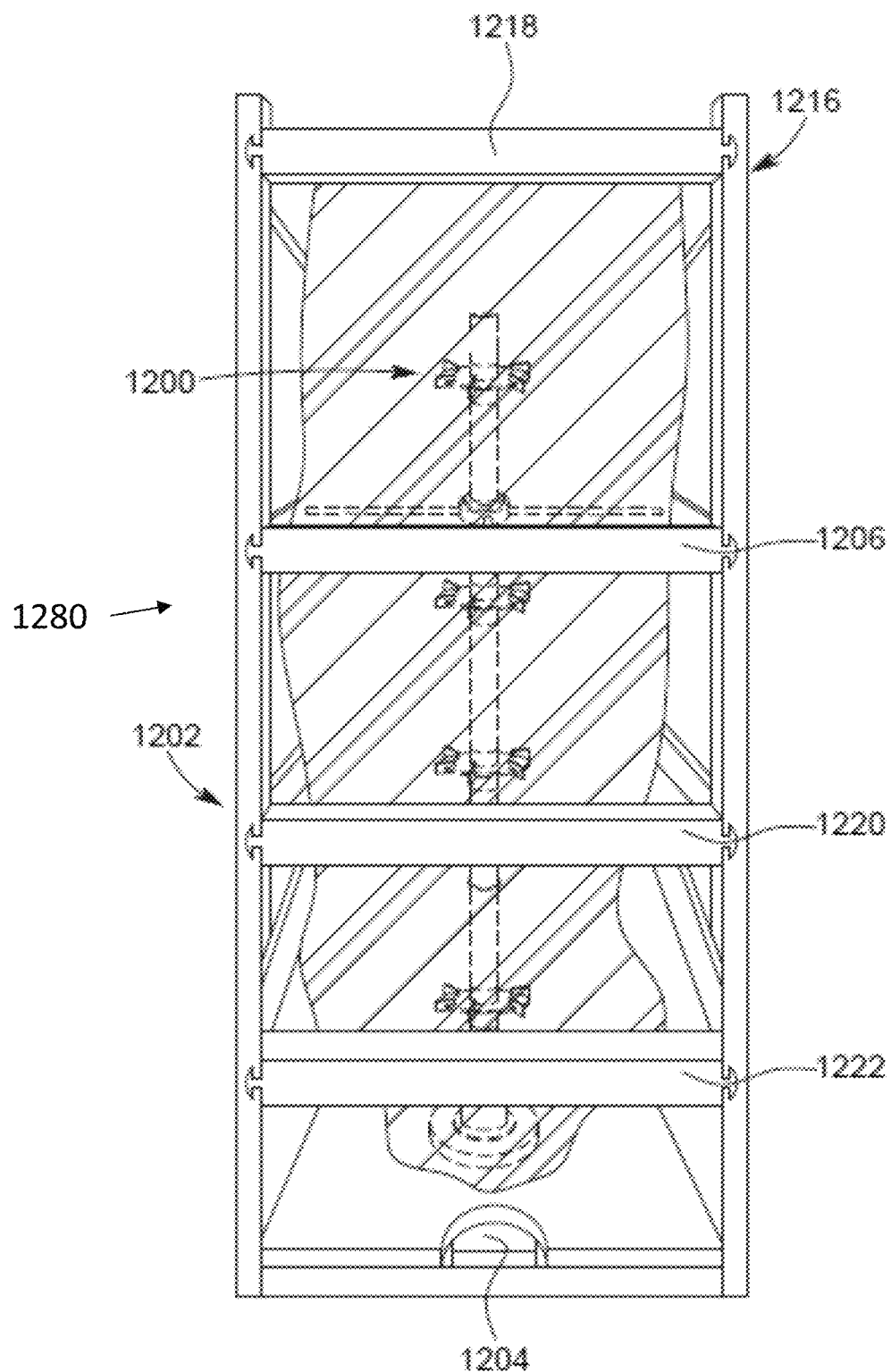
FIGS. 12A and 12B are front perspective views of a bioreactor vessel and open frame structure.
Figure 12B:
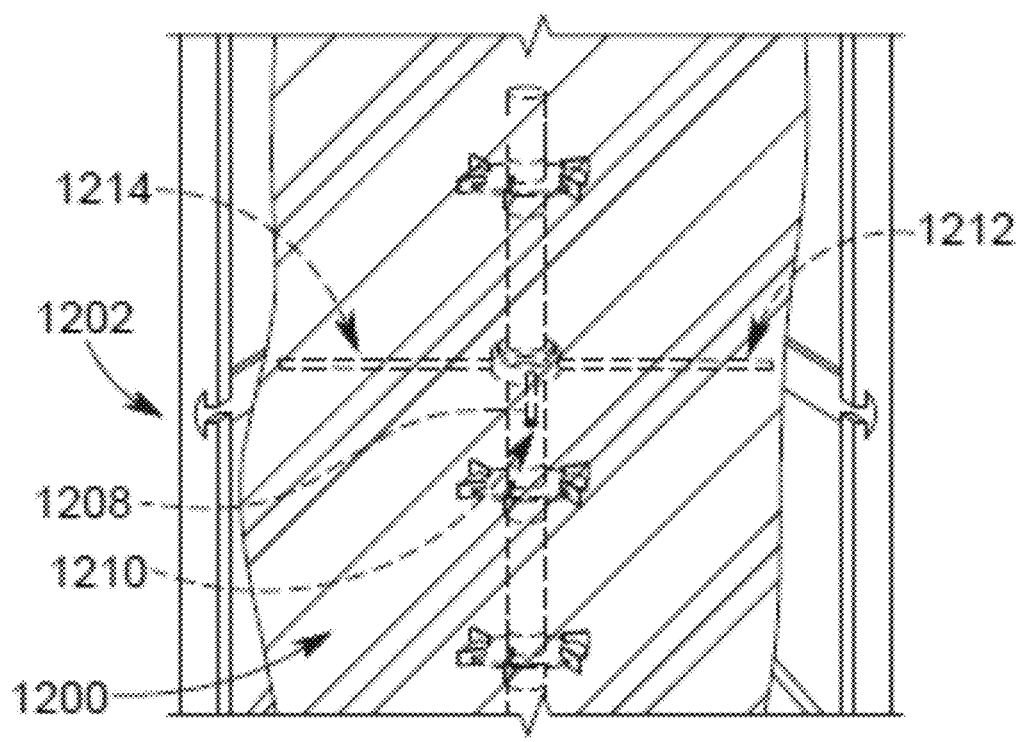

In one embodiment, the container may be shipped after sterilization. With such an embodiment, unpacking the vessel may be accomplished so as to maintain the sterility of the container as shown, for example, as shown in FIG. 12A and FIG. 12B. Both FIG. 12A and FIG. 12B show packaging 1280 including vessel 1200 positioned in open frame structure 1202. After the surrounding packing materials (e.g., double polypropylene bags referred to above) have been removed including for example, a plastic enclosure around the open frame and cable ties used to secure various vessel components (e.g., feed lines, tubing, probe and sensor lines) to the open frame structure, the slide clip 1204 and front cross member 1206 as shown in FIG. 12A are removed. As a result, shown in FIG. 12B support structure rod 1208 may be removed through orifice 1210 in container 1200. Support rods 1212 and 1214 may then be lifted to release them from the open frame structure 1200 and removed in a similar manner. Top back cross bar 1216 and front cross members 1218, 1220 and 1222 shown in FIG. 12A may then be removed. Upon the completion of the removal of top back cross bar 1216, front cross bars 1206, 1218, 1220 and 1222, slide clip 1204 and support rods 1208, 1212 and 1214, container 1200 can be removed from open frame structure 1202 with minimal compromise to its sterile condition. Top back cross bar 1216 and front cross bars 1206, 1218 and 1220 as well as the other parts of open frame structure 1202 may be connected using, for example, tongue and pocket interlocking features. Furthermore, One of the main advantages of this packaging is that the assembly of the double bagged open frame structure with vessel therein is cleanroom compatible. Also the entire foam structure being double-bagged help facilitate easily passage of the assembly through a material airlock and to the bioreactor clean-room. A user can, therefore, bring the assembly to the bioreactor itself before completing the unpacking process, thus minimizing damage or sanitary compromise to the bag due to handling. For example, features such as the removable cross-members, support rods and slide clip allow easy tool-free disassembly and instillation at the bioreactor, which is completed by lifting the vessel from the packaging material into the bioreactor. As a result, the vessel is maintained in a controlled protective environment from the manufacturer to the point of installation and use in the bioreactor.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A packaging for storage and transport of a bioreactor system,
   the bioreactor system having a vessel comprising a flexible material defining a chamber and a mixing system disposed in the chamber, the mixing system including a base and a shaft rotatably mounted in the base,
   the packaging comprising:
   a frame comprising a base member including a cavity configured in size to have the mixing system base securely positioned therein, vertical support members connected to the base member, and cross members connecting adjacent vertical support members; and
   a support structure connected to the frame and configured to support the shaft of the mixing system, wherein the support structure comprises a plurality of rods each connected to the frame and each connected to a hub rotatably positioned around the shaft.

2. The packaging of claim 1, wherein the vessel's flexible material includes a plurality of orifices and tubing sections having first and second ends, each orifice connected to the first end of one of the plurality of tubing sections that extends from each orifice into the vessel's chamber and the second end is connected to the hub, the connections of the orifice to the first end of the one of the plurality of tubing sections and of the second end of the one of the plurality of tubing sections to the hub are capable of substantially preventing fluid leakage; and each of said plurality of rods are disposed in one of the plurality of tubing sections.

3. The packaging of claim 2, wherein the tubing sections are flexible material.

4. The packaging of claim 1, further including a slide clip that is positioned in the cavity of the base member and is capable of being magnetically attached to the mixing system base.

5. The packaging of claim 1, further comprising the frame including a top section, a base section and sides; and external packing including:
   a top tray that is positioned adjacent the top section of the frame, and
   a bottom tray that is positioned adjacent the base section of the frame and sides positioned adjacent the sides of the frame.

6. The packaging of claim 5, further comprising a shipping pallet on which the bottom tray is positioned and at least one shipping strap to secure the packaging and external packing to the shipping pallet.

7. A packaging for storage and transport of a bioreactor system,
   the bioreactor system having a vessel comprising a flexible material defining a chamber and a mixing system disposed in the chamber, the mixing system including a base and a shaft rotatably mounted in the base,
   the packaging comprising:
   a frame comprising a base member including a cavity configured in size to have the mixing system base securely positioned therein and vertical support members connected to the base member, and cross members connecting adjacent vertical support members; and
   a support structure connected to the frame and configured to be connected to the shaft of the mixing system
   wherein the frame includes 4 vertical support members defining a front side, a left side, a right side and a back side; 4 front side cross members, 3 left side cross members, 3 right side cross members and 3 back side cross members such that an open space is defined in the frame of a suitable size to allow the vessel to be positioned in the open space.

8. The packaging of claim 7, wherein the front side cross members are elongated defining two ends and including a tongue portion at each end and the vertical support members to which the front side member is attached include a pocket of a complementary shape to the tongue portion so as to provide a substantially snug fit when the tongue portion is positioned in the pocket.

* * * * *